United States Patent [19]
Alfano et al.

[11] Patent Number: 5,902,110
[45] Date of Patent: May 11, 1999

[54] BONE REGENERATION

[75] Inventors: Michael C. Alfano, Franklin Lakes; Emanual S. Troullos, Baskin Ridge, both of N.J.

[73] Assignee: The Block Drug Company, Jersey City, N.J.

[21] Appl. No.: 08/962,856

[22] Filed: Nov. 3, 1997

Related U.S. Application Data

[63] Continuation of application No. 08/574,054, Dec. 18, 1995, abandoned.

[51] Int. Cl.[6] ...................................................... A61C 5/00
[52] U.S. Cl. ............................. 433/215; 424/54; 514/900
[58] Field of Search ........................ 424/54, 439; 514/49, 514/900; 433/215

[56] References Cited

U.S. PATENT DOCUMENTS

| | | | |
|---|---|---|---|
| 4,894,232 | 1/1990 | Reul et al. | 424/439 |
| 5,190,981 | 3/1993 | Wechter | 514/902 |
| 5,465,609 | 11/1995 | Kelm et al. | 424/54 |

FOREIGN PATENT DOCUMENTS

| | | | |
|---|---|---|---|
| 1376680 | 8/1984 | European Pat. Off. | |
| 0137668 | 4/1985 | European Pat. Off. | 514/900 |

OTHER PUBLICATIONS

Oates, J.A. & Wood, A.J. Nonsteroidal Antiinflammatory Drugs—Differences and Dimilarities, New England Journal of Medicine Jun. 13, 1997.

Yazdi, M., Cheung, D.T., Cobble, S. Nimmi, M.E. & Schonfeld, S.E. Effects of nonsteroidal antiinflammatory drugs on demineralized bone–induced bone formation J. Periodont. Res. 1992: 27: 28–33.

Jeffcoat, M.K., Reddy, M.S., Wang, I.C., Meuninghoff, L.A., Farmer, J.B. & Koth, D.L., The Effect of Systemic Flurbiprofen on Bone Supporting Dental Implants JADA, vol. 126, Mar. 1995.

Nishimura, I., Sxabo, G., Flynn, E. & Atwood, D.A. A Local pathophysiologic mechanism of the resorption of residual ridges: Prostaglandin as a mediator of bone resorption. The Journal of Prosthetic Dentistry vol. 60 (3) Sep. 1988.

*Primary Examiner*—John J. Wilson
*Attorney, Agent, or Firm*—Craig M. Bell; Dann, Dorfman, Herrell and Skillman

[57] ABSTRACT

A method for reducing bone resorption at tooth extraction sites by topically applying a prostaglandin inhibitor, such as a non-steroidal anti-inflammatory drug (NSAID) to the affected area. The preferred NSAID is ketoprofen. The composition may also include a penetration enhancer such as vitamin E.

6 Claims, No Drawings

BONE REGENERATION

This is a continuation of application Ser. No. 08/574,054, filed Dec. 18, 1995, now abandoned.

BACKGROUND OF THE INVENTION

1. Field of the Invention

The invention relates to methods and compositions for encouraging bone regeneration, especially after tooth loss, using non-steroidal anti-inflammatory drugs (NSAIDs).

2. Description of Related Art

Removing a tooth in dentistry can have consequences that extend far beyond the loss of the tooth. Resorption of the residual alveolar ridge that formerly supported the tooth is a chronic localized process that occurs following tooth extraction. This bone loss can affect nearby, healthy teeth and can increase the difficulty of fitting dentures and supporting other replacement dental work. Although the rate of bone loss is most rapid shortly after tooth extraction, resorption may continue long after the extraction.

Removing a tooth for the purpose of fitting full or partial dentures is a procedure that can often be planned in advance. Therapy can begin even before removal of the tooth or teeth. Extraction mandated by trauma or other emergency conditions, however, often cannot be planned far in advance, so pre-extraction therapy is not always possible.

Resorption is an especially difficult problem for fitting dentures. Stability, retention, function and the aesthetics of removable dentures are directly affected by alveolar ridge size and shape. Thus, resorption is an important factor in determining the longevity and clinical outcome of a removable denture.

Bone resorption is also a difficult problem around dental implants, particularly during the initial loading period.

Often, two different types of dentures are used with a patient. An "immediate" denture is a removable denture inserted on the day of tooth extraction. Its purpose is to restore function and alleviate the embarrassment that can occur when the patient is forced to endure an extended period of time without teeth. "Conventional" dentures are fitted later, after initial healing, and are intended to be longer-lasting. Bone loss can have a deleterious effect on the fit and efficacy of both types of dentures. Immediate dentures may need to be refitted by the dentist as soon as a few months after the extraction, and conventional, permanent dentures may need frequent monitoring and alteration or replacement.

Although many dentists do nothing at all to forestall bone loss, those that do treat bone loss after extraction do so by placing a material in the post-extraction socket that at least discourages resorption. These materials include bone from cadavers, hydroxyapatite, and specially processed glass particles.

Bone is difficult to work with and, if not properly treated, can carry disease vectors from the donor. Hydroxyapatite is difficult to work with and tends to migrate away from the site. Bioactive glass is an intriguing new product on the market and, although it does not suffer from the problems of the other materials, it has not yet gained wide acceptance in the dental market.

Implanted materials have one additional drawback. At best, the materials act as a matrix for bone growth. They do nothing to reduce or eliminate the forces that cause resorption in the first place. Thus there is still a need in the art for a material that, either alone or in combination with an implanted material, acts to reduce the forces that encourage bone resorption after tooth extraction. A special need remains in the art for a bone-loss therapy that can be administered during or after tooth loss, in those instances when pre-extraction therapy is unavailable.

Various studies have been carried out on bone formation using non-steroidal anti-inflammatory drugs as agents affecting bone growth and bone structure. One article, Yazdi, M. et al., "Effects of nonsteroidal anti-inflamatory drugs on Demineralized Bone-induced Bone Formation," J. Periodont Res 1992; 27:28–33, reported the effects of acetylsalicylic acid, acetarninophen, ibuprofen, indomethacin, prioxicam and flurbiprofen on bone growth over powdered demineralized bone implanted into para-sternal sites on rats. The various additives (as well as the control) were injected into the rats in a single daily subcutaneous injection beginning either three days prior to implantation or three days after implantation. The researchers reported that both inhibitory and stimulatory effects on bone formation were found in rats treated before implantation. Despite some encouraging pictures in the article, the researchers concluded that pretreating with flurbiprofen "did not appear to significantly affect bone formation," id. at 31, while pretreatment with ibuprofen appeared to enhance bone formation. Id. at 31–32. Treating with NSAIDS after implantation, however, did not appear to affect the rats, "Wile no significant differences between experimental and control groups were observed, there was good osteoinduction in groups treated with indomethacin . . . piroxicam . . . or flurbiprofen . . . " Id. at 32.

Another research group studied the effects of systemic flurbiprofen on dental implants, Jeffcoat, M. et al., "The Effect of Systemic Flurbiprofen on Bone Supporting Dental Implants," JADA, Vol. 126, March 1995, 305–11. The group noted that flurbiprofen, along with others, had shown the ability to retard alveolar bone loss due to periodontitis but that the effect of NSAIDS on preventing bone loss in implant situations had not been established. The researchers studied the effect of a course of systemic administration of flurbiprofen on titanium implants using 50 and 100 mg doses of flurbiprofen. The high dose flurbiprofen dosage reduced bone loss, but showed no increase in bone levels, except for a brief increase in bone mass after three months that subsequently disappeared. The researchers concluded, "At first glance, the hypothesis underlying the effect(s) of NSAIDs on bone may appear deceptively straightforward. However, the basic pathophysiology underlying these agents could be used to support either positive or negative effects on bone." Id. at 310.

SUMMARY OF THE INVENTION

The principal object of the present invention therefore is to provide an agent for reducing the resorption of bone after tooth extraction.

Another object of the invention is to provide an agent for reducing the resorption of bone after tooth extraction that may be used in conjunction with implants or that may be used in conjunction with immediate dentures. Still another object of the invention is to provide a topically administered product for reducing bone loss that may be applied by the patient, without strict measurement or oversight by the dentist. Another object of the invention is to provide a therapy for post-extraction bone loss that may be administered after extraction takes place.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides a combination of an anti-inflammatory agent and a penetration enhancer for application to the site of an extracted tooth. These ingredients combat bone loss, and they alleviate pain.

To further achieve the foregoing objects and in accordance with the purpose of the invention, the invention further provides a method for reducing or preventing bone loss after tooth extraction comprising the step of topically applying an anti-inflammatory drug to the site of an extracted tooth. This step of topical application may be carried out by applying a creme, gel, lotion or other delivery vehicle containing the active ingredients to the environs of an extracted tooth or implant directly or by applying the delivery vehicle to a denture or other dental work covering the site, or by impregnating an implant material with the active ingredients.

DESCRIPTION OF THE PREFERRED EMBODIMENTS

Reference will now be made in detail to the presently preferred embodiments of the invention.

One of the first responses of the human body to tooth extraction is inflammation of the site. While inflammation is part of the wound repair mechanism, several mediators released at the site of cell injury can stimulate bone resorption. One of these recognized mediators is prostaglandin $E_2$ ($PGE_2$). It has been shown that the prostaglandin inhibitor indomethacin inhibits bone resorption, presumably by prostaglandin inhibition. Nishimura, I. et al., "A Local Pathophysiologic Mechanism of the Resorption of Residual Ridges: Prostaglandin as a Mediator of Bone Resorption," *The Journal of Prosthetic Dentistry*, vol. 60, No. 3, pp. 381–388 (September 1988). (Although this article mentions both indomethacin and flurbiprofen, only indomethacin was tested.)

Bone resorption after extraction differs from other conditions because there is an acute injury followed by a lengthy period of wound repair. After tooth extraction, a sequence of physiologic events occurs involving clot formation, connective tissue repairs, osteoid formation and bone remodeling. Thus post extraction bone loss occurs in an environment of bone repair, whereas alveolar bone loss due to periodontal disease is the result of a chronic, bacterially-mediated destructive process.

To combat bone resorption, the invention contemplates topical administration of a non-steroidal anti-inflammatory drug (NSAID) to the area affected by extraction of the tooth or by an implant. This topical administration may be carried out in a number of ways. The NSAID may be applied as a topical cream or ointment to the surface of the affected area. It may be applied to the surface of the dental prosthesis placed over the site of the extraction, either as a separate ointment or as part of a denture adhesive cream or powder. Preferably, the NSAID is applied fairly frequently during the early phases of recovery from tooth extraction, although less frequent applications may be appropriate thereafter. As will be understood by those skilled in the art, sustained release or other technologies may be employed to affect the release profile of the NSAID to the affected site.

Another delivery system for the NSAID is incorporation into an implant placed into the affected site. Over time, the NSAID will migrate out of the implant and into the surrounding tissue. Although this method is probably not the most effective method for delivering large amounts of NSAID into the tissue in a short time, the method is an effective long term treatment.

The preferred non-steroidal anti-inflammatory drug of the invention is ketoprofen, although other non-steroidal anti-inflammatory drugs such as ibuprofen or flurbiprofen may be substituted for ketoprofen. Indeed, any prostaglandin inhibitor may be substituted for ketoprofen.

The NSAID may be delivered in any vehicle that is both capable of delivering the NSAID and not overly injurious to the oral environment. The delivery system may be as simple as an aqueous solution or suspension of the NSAID, or the system may be an ointment or cream made from ingredients well known in the art.

Of course, the NSAID) will be more effective if it penetrates more fully into the target tissues. Accordingly, one embodiment of the invention comprises the combination of an NSAID and a penetration enhancer to carry the NSAID to the target site to inhibit bone resorption associated with an extracted tooth.

Preferred penetration enhancers include known penetration enhancers. Especially preferred are Vitamin E and its analogs, which act to transport the NSAID to the active site without causing systemic effects.

The invention may be made by mixing a therapeutic amount of the NSAID in a conventional cream, gel or other topical medium. Preferably, the NSAID comprises up to about 5% by weight of the cream or gel, and more preferably up to about 3% by weight. If desired, a penetration enhancer may also be added in appropriate amounts. The preferred penetration enhancer is Vitamin E, and the preferred amount of Vitamin E is up to about 0.3% of the cream or gel by weight. Higher levels of Vitamin E may be used, but higher levels do not appear to improve the penetration of the NSAID. Of course, different penetration enhancers may have different levels of efficacy, and more or less of another penetration enhancer may be required.

The preferred embodiments of the invention will be made more clear by reference to the following Examples.

EXAMPLES

Application of ketoprofen gel into maxillary dentures was studied in volunteer edentulous subjects. One gram of either placebo or 3% ketoprofen gel was applied inside the denture each morning and evening over a twenty-four (24) week test period. In one test cell straight 3% ketoprofen gel was used, in a second cell a placebo was used, and in a third cell, ketoprofen gel was used for a period of four weeks and then placebo was used for 20 weeks.

The formulation for the ketoprofen gel contained 3% ketoprofen in a pluronic/water gel base. Polycarbophil was added as a mucosal adhesive, vitamin E was added as a penetration enhancer, and the gel was adjusted to a pH within the range of 4.5 to about 7.0.

Intra-oral Radiographs were taken at day 84 and day 168 of treatment, and the change in bone height was measured in pixels of a digitized image of the radiograph. The number of patients, the mean, the standard deviation, the median and the range were recorded and were set out in Table 1. The same figures were also calculated on a percentage basis and are also set forth in Table 1.

The results obtained in Table 1 show that there is a significant reduction in bone resorption, even for the partial treatment.

TABLE 1

Summary Statistics and Analysis of Ketoprofen Gel for Oral Use

| Properties Measured | 3% ketoprofen gel for 6 months | 3% ketoprofen gel for 1 month | Placebo | P value for overall treatment | P value for Col.1 v. Col.2 | P value for Col.1 v. Col.3 | P value for Col.2 v. Col.3 |
|---|---|---|---|---|---|---|---|
| Change in Bone Height (measured in pixels of intraoral radiograph) Day 84 | N = 10<br>Mean = 10.30<br>Std. Dev. = 6.563<br>Med. = 8.66<br>Range = 0.00–24.19 | N = 12<br>Mean = 13.28<br>Std. Dev. = 7.821<br>Med. = 13.36<br>Range = 3.16–26.08 | N = 9<br>Mean = 18.05<br>Std. Dev. = 9.757<br>Med. = 13.34<br>Range = 7.62–34.01 | ≦0.05 | 0.396 | 0.046 | 0.191 |
| Change in Bone Height (measured in pixels of intraoral radiograph) Day 168 | N = 10<br>Mean = 16.76<br>Std. Dev. = 6.152<br>Med. = 16.34<br>Range = 6.08–27.66 | N = 11<br>Mean = 20.14<br>Std. Dev. = 11.844<br>Med. = 22.00<br>Range = 4.12–46.00 | N = 9<br>Mean = 25.72<br>Std. Dev. = 10.570<br>Med. = 26.08<br>Range = 10.05–41.01 | ≦0.05 | 0.440 | 0.059 | 0.220 |
| Change in Bone Area (on a percentage basis) Day 84 | N = 10<br>Mean = 21.94<br>Std. Dev. = 10.806<br>Med. = 18.67<br>Range = 8.11–45.78 | N = 12<br>Mean = 23.75<br>Std. Dev. = 17.400<br>Med. = 18.90<br>Range = 1.890–64.56 | N = 9<br>Mean = 38.67<br>Std. Dev. = 21.386<br>Med. = 29.22<br>Range = 16.00–78.56 | ≦0.05 | 0.804 | 0.040 | 0.056 |
| Change in Bone Area (on a percentage basis) Day 168 | N = 10<br>Mean = 33.68<br>Std. Dev. = 16.02<br>Med. = 29.45<br>Range = 15.45–67.45 | N = 11<br>Mean = 31.71<br>Std. Dev. = 24.129<br>Med. = 30.89<br>Range = 5.110–86.00 | N = 9<br>Mean = 49.99<br>Std. Dev. = 19.368<br>Med. = 49.78<br>Range = 22.00–89.89 | ≦0.05 | 0.826 | 0.092 | 0.055 |

As shown in Table 1, topical treatment with ketoprofen provides significant benefits in treating bone resorption on extraction sites even if the treatment is only relatively short term. A longer term course of therapy may be even more beneficial and is the preferred form of treatment. None of the prior art would have suggested such a dramatic effect of topical application of an NSAID such as ketoprofen on the alveolar bone level of humans subjected to tooth extraction trauma.

The purpose of the above description is to illustrate some embodiments of the present invention without implying a limitation. It will be apparent to those skilled in the art that various modifications and variations may be made in the apparatus or procedure of the invention without departing from the scope or spirit of the invention.

What is claimed is:

1. A method for reducing bone resorption in tooth extraction or implant sites comprising the step of topically applying a therapeutic amount of a composition comprising ketoprofen and a penetration enhancer to the site of the tooth extraction or implant.

2. The method of claim 1, wherein said penetration enhancer is selected from the group consisting of vitamin E and its analogs.

3. The method of claim 1, wherein said composition is applied to the surface of a denture or other prosthetic device that is to be exposed to the site of a tooth extraction or implant.

4. The method of claim 3, wherein said composition comprises a denture adhesive or powder.

5. The method of claim 1, wherein said therapeutic amount is applied after extraction of the tooth.

6. The method of claim 1, wherein said therapeutic amount is applied periodically to the site of the tooth extraction or implant.

* * * * *